United States Patent
Naiki et al.

(10) Patent No.: US 10,004,716 B2
(45) Date of Patent: Jun. 26, 2018

(54) THERAPEUTIC/ PREVENTIVE AGENT CONTAINING COUMARIN DERIVATIVE AS ACTIVE INGREDIENT

(71) Applicant: NIPPON ZOKI PHARMACEUTICAL CO., LTD., Osaka-shi, Osaka (JP)

(72) Inventors: Mitsuru Naiki, Kato (JP); Takumi Numazawa, Kato (JP); Hiroki Fujisawa, Osaka (JP)

(73) Assignee: NIPPON ZOKI PHARMACEUTICAL CO., LTD., Osaka-shi (JP)

( * ) Notice: Subject to any disclaimer, the term of this patent is extended or adjusted under 35 U.S.C. 154(b) by 11 days.

(21) Appl. No.: 15/127,618

(22) PCT Filed: Mar. 19, 2015

(86) PCT No.: PCT/JP2015/058237
§ 371 (c)(1),
(2) Date: Sep. 20, 2016

(87) PCT Pub. No.: WO2015/141775
PCT Pub. Date: Sep. 24, 2015

(65) Prior Publication Data
US 2017/0135985 A1    May 18, 2017

(30) Foreign Application Priority Data

Mar. 20, 2014 (JP) .................................. 2014-058336

(51) Int. Cl.
| | |
|---|---|
| A61K 31/37 | (2006.01) |
| A61K 9/00 | (2006.01) |
| A61K 31/635 | (2006.01) |
| A61K 31/4433 | (2006.01) |
| A61K 31/381 | (2006.01) |

(52) U.S. Cl.
CPC .............. *A61K 31/37* (2013.01); *A61K 9/007* (2013.01); *A61K 31/381* (2013.01); *A61K 31/4433* (2013.01); *A61K 31/635* (2013.01)

(58) Field of Classification Search
CPC ...................................................... A61K 31/37
See application file for complete search history.

(56) References Cited

U.S. PATENT DOCUMENTS

| | | |
|---|---|---|
| 2008/0020068 A1 | 1/2008 | Germer et al. |
| 2008/0153872 A1 | 6/2008 | Mercep et al. |
| 2015/0232440 A1 | 8/2015 | Naiki et al. |

FOREIGN PATENT DOCUMENTS

| | | |
|---|---|---|
| EP | 2899187 A1 | 7/2015 |
| JP | 2008/505064 A | 2/2008 |
| JP | 2008/526951 A | 7/2008 |
| WO | 2006/111858 A2 | 10/2006 |
| WO | 2010/055384 A1 | 5/2010 |
| WO | 2012/079020 A2 | 6/2012 |
| WO | 2014/046224 A1 | 3/2014 |

OTHER PUBLICATIONS

"5 Best Ways to Prevent COPD." © 2017. Available from: < https://www.everydayhealth.com/copd/5-best-ways-to-prevent-copd.aspx >.*
"Pulmonary Fibrosis." © 2017. Available from: < http://www.healthline.com/health/pulmonary-fibrosis >.*
"Degenerative Disc Disease Treatment, Prognosis, Prevention." © 2007. Available from: <http://www.healthcommunities.com/degenerative-disc-disease/treatment.shtml >.*
Jun. 16, 2016 Written Opinion issued in International Application No. PCT/JP2015/058237.
Sep. 20, 2016 International Preliminary Report on Patentability issued in International Application No. PCT/JP2015/058237.
Science Culture, Jan. 1965 vol. 31, No. 1 p. 27.
Science Culture, Jan. 1971 vol. 37, No. 1 pp. 58-59.
Jun. 16, 2015 Search Report issued in International Patent Application No. PCT/JP2015/058237.
Feb. 8 , 2017 Search Report issued in European Patent Application No. 15764236.4.

* cited by examiner

*Primary Examiner* — Noble E Jarrell
*Assistant Examiner* — John S Kenyon
(74) *Attorney, Agent, or Firm* — Oliff PLC

(57) ABSTRACT

A method for prophylactically or therapeutically treating an inflammatory disease and/or degenerative intervertebral disk disease in a subject is disclosed. The method includes administering to the subject an effective amount of a coumarin derivative represented by formula (I), or a pharmaceutically acceptable salt or hydrate thereof:

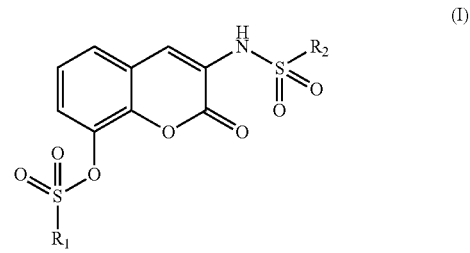

(I)

Each of R1 and R2 is independently (a) phenyl optionally substituted with alkoxy, alkyl, cyano, nitro, hydroxy, trifluoromethyl, amino, carboxy, alkoxycarbonyl, phenyl, or one or two halogen(s), (b) pyridyl, (c) alkyl, or (d) thienyl.

13 Claims, No Drawings

US 10,004,716 B2

THERAPEUTIC/ PREVENTIVE AGENT CONTAINING COUMARIN DERIVATIVE AS ACTIVE INGREDIENT

TECHNICAL FIELD

The present invention relates to a preventive or therapeutic agent for inflammatory disease or degenerative intervertebral disk disease.

BACKGROUND ART

Inflammation is a defensive mechanism which is inherent in the living body for an effective removal of pathogens and injured tissues. In the inflammation, various transmitters are released from cells and the symptoms such as swelling, pain and fever are accompanied therewith. A transient inflammation is necessary for the protection of living body while, on the other hand, uncontrolled inflammation causes injury of tissues and becomes a fundamental cause for various diseases. Inflammatory disease is a general term for the diseases induced by a transmitter by the inflammation reaction and examples thereof are asthma, chronic obstructive pulmonary disease (COPD), pulmonary fibrosis, allergic disease, autoimmune disease, rhinitis, gastroenteritis, hepatitis, pancreatitis, nephritis, cystitis, enteritis, inflammatory pain, arterial sclerosis, dermatitis, myositis, vasculitis, inflammatory eye disease and multiple sclerosis. It has been said that inflammation is induced and adjusted by a complicated interaction between lipid mediators such as prostaglandin and leukotriene and inflammatory cytokine and chemokine released from inflammatory cells (such as mast cell, basophile, endothelial cell, macrophage and neutrophile). It has been known that, in the initial step of the inflammation, increase in blood vessel permeability, activation of endothelial cells and infiltration of inflammatory cells happen responding to local inflammation-inducing signal and that inflammatory cytokines [such as interleukin (IL)-$1\beta$, IL-6, IL-8, interferon (IFN)-$\gamma$ and tumor necrotic factor (TNF)-$\alpha$], chemokine and lipid mediators play a central role therein. On the other hand, degenerative intervertebral disk is induced by participation of various factors such as aging, mechanical stress, smoking and genetic factor. Intervertebral disk comprises the gel-like nucleus pulposus abundant in water and the annulus fibrosus surrounding the same and age-related changes of the intervertebral disk start from second half of the teenage where water content and proteoglycan content in the nucleus pulposus decrease. As a result, the intervertebral disk results in degeneration such as a decrease in elasticity and a decrease in volume and the degenerated tissues have poor natural recovering property whereby it is the current status that no effective therapeutic method is available. When degenerative intervertebral disk happens, it stimulates the nerves around the intervertebral disk or it applies the burden to ligament, joint and muscle whereupon it may cause the lumbago. As to the factors for the inhibition of synthesis of proteoglycan in nucleus pulposus inducing the degenerative intervertebral disk, there are listed a decrease in oxygen supply to intervertebral disk by smoking in addition to an excessive mechanical stress. Examples of the disease induced by degenerative intervertebral disk are lumbar intervertebral disk disease and degenerative scoliosis. As to the symptom of those diseases, symptoms such as numbness of lower limbs and muscle weakness may happen in addition to pain and, when they worsen, daily life is disturbed. Because non-steroidal anti-inflammatory drug (NSAID) and cyclooxygenase (COX)-2 inhibitor which are used mainly for the treatment of inflammatory diseases and degenerative intervertebral disk diseases have a side effect to stomach, intestine and cardiovascular system as well as an anti-inflammatory effect and an analgesic effect, there has been a brisk demand in clinical sites for novel drugs showing excellent effect with less side effect.

In view of the fact that a certain coumarin derivative has anti-inflammatory action and suppressive action for degenerative intervertebral disk, the present inventors have found that such a derivative is useful as a preventive or therapeutic agent for inflammatory disease and degenerative intervertebral disk disease. As to the coumarin derivative, compounds where 3-position of a coumarin skeleton is substituted with a sulfonylamino group are disclosed in Non-Patent Documents 1 and 2. However, those documents merely report that the compounds as such are synthesized and there is no description therein at all that they have a pharmacological action.

PRIOR ART DOCUMENTS

Non-Patent Documents

Non-Patent Document 1: Science and Culture, vol. 31, no. 1, page 27, 1965
Non-Patent Document 2: Science and Culture, vol. 37, no. 1, pages 58 to 59, 1971

SUMMARY OF THE INVENTION

Problem that the Invention is to Solve

The problem of the present invention is to provide a preventive or therapeutic agent for inflammatory disease and degenerative intervertebral disk disease.

Means for Solving the Problem

The inventors have conducted extensive studies in order to solve the above problem and, as a result, a coumarin derivative represented by the formula (I) or a pharmaceutically acceptable salt or hydrate thereof (Hereinafter, they will be also referred to as "the present compound". In addition, even such a case where just a word "compound" is used, it sometimes includes a pharmaceutically acceptable salt or hydrate thereof.) exhibits an excellent pharmacological action such as suppression of expression of inflammatory cytokine as well as suppression of activation of transcription factor and is useful as a preventive or therapeutic agent for inflammatory disease or degenerative intervertebral disk disease whereupon the present invention has been accomplished. In the meanwhile, the inventors have also found separately from the present invention that the present compound is useful as a preventive or therapeutic agent for arthropathy (such as osteoarthrosis and rheumatoid arthritis) (PCT/JP2013/075414). Accordingly, the "inflammatory disease" mentioned hereinafter in this application shall not include "arthropathy".

Effect of the Invention

The coumarin derivative represented by the following formula (I), or a pharmaceutically acceptable salt or hydrate thereof (the present compound) has shown an excellent suppressive action in various pharmacological tests concerning inflammation and degenerative intervertebral disk.

Because of this, the present compound is highly useful as a preventive or therapeutic agent for inflammatory disease such as asthma or hepatitis and degenerative intervertebral disk disease. Incidentally, the terms "preventive" and "therapeutic" in this application covers such a meaning where symptom of the disease is alleviated, mitigated or ameliorated.

EMBODIMENTS FOR CARRYING OUT THE INVENTION

The present invention relates to a preventive or therapeutic agent for inflammatory disease and degenerative intervertebral disk disease containing at least one member of the coumarin derivative represented by the following formula (I), and a pharmaceutically acceptable salt and hydrate thereof (the present compound) as an active ingredient.

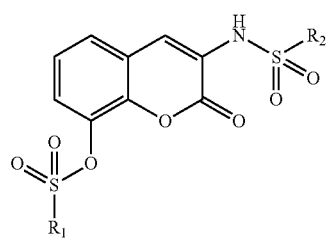

(I)

[In the formula, $R_1$ and $R_2$ are the same or different, and are (a) phenyl which may be substituted with alkoxy, alkyl, cyano, nitro, hydroxy, trifluoromethyl, amino, carboxy, alkoxycarbonyl, phenyl or one or two halogen(s), (b) pyridyl, (c) alkyl or (d) thienyl.]

In the substituent of the above formula (I), the alkyl is preferably a linear or branched alkyl having 1 to 4 carbon(s) such as methyl, ethyl, propyl, isopropyl, butyl, isobutyl, sec-butyl or t-butyl.

The alkoxy is preferably a linear or branched alkoxy having 1 to 4 carbon(s) such as methoxy, ethoxy, n-propoxy, isopropoxy, n-butoxy, isobutoxy, sec-butoxy or t-butoxy.

The halogen is fluorine, chlorine, bromine, iodine or the like.

As hereunder, general method for producing the present compound is shown. However, in producing a specific compound, it is a matter of course that persons skilled in the art are able to appropriately modify the method depending upon the chemical structure thereof.

A compound of the formula (I) is able to be produced by a sulfonylamidation reaction of a compound of the formula (II). For example, the sulfonylamidation reaction may be conducted for the compound of the formula (II) and a substituted benzenesulfonyl halide in pyridine or a basic solvent at an appropriate temperature between room temperature and boiling point of the solvent.

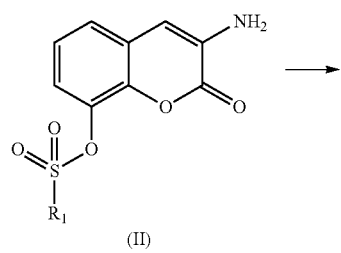

(II)

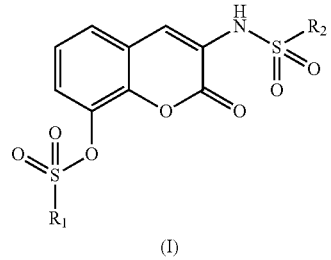

(I)

A compound of the formula (II) is prepared by an acid hydrolysis reaction of a compound of the formula (III). For example, the acid hydrolysis reaction can be conducted in a mixed solvent of an organic acid such as acetic acid with sulfuric acid adjusted to an appropriate concentration at an appropriate temperature preferably from room temperature to boiling point of the solvent.

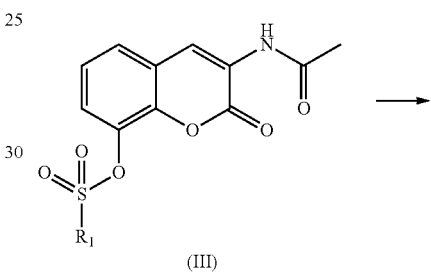

(III)

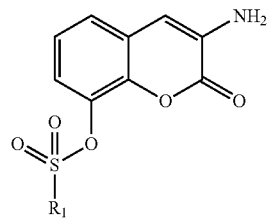

(II)

A compound of the formula (III) is prepared by a sulfonyl esterification reaction of a compound (IV) of the formula (IV). For example, the sulfonyl esterification reaction can be conducted using a compound of the formula (IV) and a substituted benzenesulfonyl halide in a basic solvent such as pyridine at advantageous temperature preferably from room temperature to boiling point of the solvent.

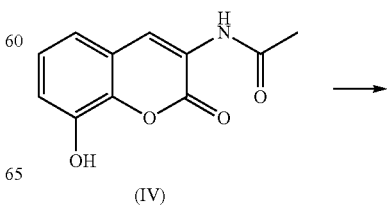

(IV)

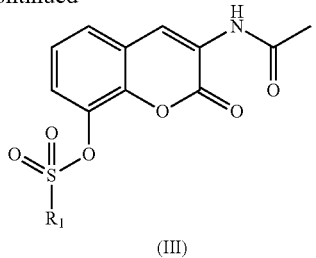

(III)

When R₁ and R₂ are the same substituent in a compound represented by the formula (I), 3-amino-2-oxo-8-hydroxychromene is subjected to a sulfonylamidation reaction and a sulfonyl esterification reaction at the same time as shown in the following Example 2 whereupon the present compound can be produced.

A compound represented by the above formula (I) includes various salts thereof when such pharmaceutically acceptable salts are available and examples thereof include an addition salt with an acid such as hydrochloric acid, sulfuric acid, nitric acid, hydrobromic acid, phosphoric acid, perchloric acid, thiocyanic acid, boric acid, formic acid, acetic acid, haloacetic acid, propionic acid, glycolic acid, citric acid, tartaric acid, succinic acid, gluconic acid, lactic acid, malonic acid, fumaric acid, anthranilic acid, benzoic acid, cinnamic acid, p-toluenesulfonic acid, naphthalenesulfonic acid or sulfanilic acid; a salt with alkali metal such as sodium or potassium, with alkali earth metal such as calcium or magnesium or with metal such as aluminum; and a salt with a base such as ammonia or an organic amine. The salts as such may be produced from each free compound by a known method or may be converted each other. Moreover, when the present compound is present in a form of a stereoisomer such as cis-trans isomer, optical isomer or structural isomer, a solvate such as hydrate or a metal complex compound, it also covers any of the stereoisomer, solvate and complex compound thereof.

Examples of the compound produced as such are shown as follows. Further, substituents corresponding to $R^1$ and $R^2$ of the above formula (I) in each compound are shown in Tables 1 and 2. With regard to the substituents $R_1$ and $R_2$ in the tables, methyl, ethyl, phenyl, pyridyl and thienyl are represented by Me, Et, Ph, Py and thienyl, respectively and, with regard to others, they are expressed using symbols of elements. Hereinafter, in referring to each compound, each of the following compound Nos. is used.

3-[(4-Methoxyphenyl)sulfonylamino]-2-oxochromen-8-yl 4-methoxybenzenesulfonate [Compound 1]
3-[(3-Methoxyphenyl)sulfonylamino]-2-oxochromen-8-yl 3-methoxybenzenesulfonate [Compound 2]
3-[(2-Methoxyphenyl)sulfonylamino]-2-oxochromen-8-yl 2-methoxybenzenesulfonate [Compound 3]
2-Oxo-3-(p-tolylsulfonylamino)chromen-8-yl 4-methylbenzenesulfonate [Compound 4]
3-(m-Tolylsulfonylamino)-2-oxochromen-8-yl 3-methylbenzenesulfonate [Compound 5]
3-(o-Tolylsulfonylamino)-2-oxochromen-8-yl 2-methylbenzenesulfonate [Compound 6]
3-[(4-Chlorophenyl)sulfonylamino]-2-oxochromen-8-yl 4-chlorobenzenesulfonate [Compound 7]
3-[(3-Chlorophenyl)sulfonylamino]-2-oxochromen-8-yl 3-chlorobenzenesulfonate [Compound 8]
3-[(2-Chlorophenyl)sulfonylamino]-2-oxochromen-8-yl 2-chlorobenzenesulfonate [Compound 9]
3-[(4-Fluorophenyl)sulfonylamino]-2-oxochromen-8-yl 4-fluorobenzenesulfonate [Compound 10]
3-[(3-Fluorophenyl)sulfonylamino]-2-oxochromen-8-yl 3-fluorobenzenesulfonate [Compound 11]
3-[(2-Fluorophenyl)sulfonylamino]-2-oxochromen-8-yl 2-fluorobenzenesulfonate [Compound 12]
3-[(4-Cyanophenyl)sulfonylamino]-2-oxochromen-8-yl 4-cyanobenzenesulfonate [Compound 13]
3-[(3-Cyanophenyl)sulfonylamino]-2-oxochromen-8-yl 3-cyanobenzenesulfonate [Compound 14]
3-[(2-Cyanophenyl)sulfonylamino]-2-oxochromen-8-yl 2-cyanobenzenesulfonate [Compound 15]
3-[(4-Nitrophenyl)sulfonylamino]-2-oxochromen-8-yl 4-nitrobenzenesulfonate [Compound 16]
3-[(3-Nitrophenyl)sulfonylamino]-2-oxochromen-8-yl 3-nitrobenzenesulfonate [Compound 17]
3-[(2-Nitrophenyl)sulfonylamino]-2-oxochromen-8-yl 2-nitrobenzenesulfonate [Compound 18]
3-[(4-Hydroxyphenyl)sulfonylamino]-2-oxochromen-8-yl 4-hydroxybenzenesulfonate [Compound 19]
3-(Benzenesulfonylamino)-2-oxochromen-8-yl 4-cyanobenzenesulfonate [Compound 20]
3-[(4-Cyanophenyl)sulfonylamino]-2-oxochromen-8-yl benzenesulfonate [Compound 21]
3-[(3-Cyanophenyl)sulfonylamino]-2-oxochromen-8-yl benzenesulfonate [Compound 22]
3-[(4-Nitrophenyl)sulfonylamino]-2-oxochromen-8-yl benzenesulfonate [Compound 23]
3-[(3-Nitrophenyl)sulfonylamino]-2-oxochromen-8-yl benzenesulfonate [Compound 24]
3-[(3-Fluorophenyl)sulfonylamino]-2-oxochromen-8-yl benzenesulfonate [Compound 25]
3-[(3,4-Difluorophenyl)sulfonylamino]-2-oxochromen-8-yl benzenesulfonate [Compound 26]
2-Oxo-3-[[4-(trifluoromethyl)phenyl]sulfonylamino]-chromen-8-yl benzenesulfonate [Compound 27]
2-Oxo-3-[[3-(trifluoromethyl)phenyl]sulfonylamino]-chromen-8-yl benzenesulfonate [Compound 28]
3-[(4-Chlorophenyl)sulfonylamino]-2-oxochromen-8-yl benzenesulfonate [Compound 29]
2-Oxo-3-[(4-phenylphenyl)sulfonylamino]chromen-8-yl benzenesulfonate [Compound 30]
3-[(3-Bromophenyl)sulfonylamino]-2-oxochromen-8-yl benzenesulfonate [Compound 31]
3-[(3-Bromophenyl)sulfonylamino]-2-oxochromen-8-yl 3-bromobenzenesulfonate [Compound 32]
2-Oxo-3-[[3-(trifluoromethyl)phenyl]sulfonylamino]-chromen-8-yl 3-(trifluoromethyl)benzenesulfonate [Compound 33]
3-(Benzenesulfonamide)-2-oxochromen-8-yl 3-bromobenzenesulfonate [Compound 34]
3-(Benzenesulfonamide)-2-oxochromen-8-yl 3-(trifluoromethyl)benzenesulfonate [Compound 35]
3-[(3-Bromophenyl)sulfonylamino)]-2-oxochromen-8-yl pyridine-3-sulfonate [Compound 36]
3-[(3-Bromophenyl)sulfonylamino)]-2-oxochromen-8-yl methanesulfonate [Compound 37]
2-Oxo-3-(3-pyridylsulfonylamino)chromen-8-yl 3-bromobenzenesulfonate [Compound 38]
3-(Methanesulfonamide)-2-oxochromen-8-yl 3-bromobenzenesulfonate [Compound 39]
3-(Methanesulfonamide)-2-oxochromen-8-yl benzene-sulfonate [Compound 40]
2-Oxo-3-[[3-(trifluoromethyl)phenyl]sulfonylamino]-chromen-8-yl 4-nitrobenzenesulfonate [Compound 41]
3-[(4-Nitrophenyl)sulfonylamino]-2-oxochromen-8-yl 3-(trifluoromethyl)benzenesulfonate [Compound 42]

3-[(3-Nitrophenyl)sulfonylamino]-2-oxochromen-8-yl thiophene-2-sulfonate [Compound 43]
2-Oxo-3-(2-thienylsulfonylamino)chromen-8-yl 3-nitrobenzenesulfonate [Compound 44]
4[8-(3-Nitrophenyl)sulfonyloxy-2-oxochromen-3-yl-sulfamoyl]benzoic acid [Compound 45]
2-Oxo-3-[[3-(trifluoromethyl)phenyl]sulfonylamino]-chromen-8-yl 4-aminobenzenesulfonate hydrochloride [Compound 46]
3-[(4-Aminophenyl)sulfonylamino]-2-oxochromen-8-yl 3-(trifluoromethyl)benzenesulfonate [Compound 47]
Ethyl 4-[3-[(3-nitrophenyl)sulfonylamino]-2-oxochromen-8-yl]oxysulfonylbenzoate [Compound 48]
4-[3-[(3-Nitrophenyl)sulfonylamino]-2-oxochromen-8-yl] oxysulfonylbenzoic acid [Compound 49]
2-Oxo-3-[[3-(trifluoromethyl)phenyl]sulfonylamino]-chromen-8-yl 3-nitrobenzenesulfonate [Compound 50]
3-[(3-(Nitrophenyl)sulfonylamino]-2-oxochromen-8-yl 3-(trifluoromethyl)benzenesulfonate [Compound 51]
2-Oxo-3-[(4-phenylphenyl)sulfonylamino]chromen-8-yl 3-(trifluoromethyl)benzenesulfonate [Compound 52]
2-Oxo-3-[(4-phenylphenyl)sulfonylamino]chromen-8-yl 3-bromobenzenesulfonate [Compound 53]
3-[(3-Bromophenyl)sulfonylamino]-2-oxochromen-8-yl 3-nitrobenzenesulfonate [Compound 54]
2-Oxo-3-[(4-phenylphenyl)sulfonylamino]chromen-8-yl 3-nitrobenzenesulfonate [Compound 55]
3-[(3-Bromophenyl)sulfonylamino]-2-oxochromen-8-yl 3-(trifluoromethyl)benzenesulfonate [Compound 56]
2-Oxo-3-[[3-(trifluoromethyl)phenyl]sulfonylamino]-chromen-8-yl 4-(trifluoromethyl)benzenesulfonate [Compound 57]
3-[(3-Bromophenyl)sulfonylamino]-2-oxochromen-8-yl 4-(trifluoromethyl)benzenesulfonate [Compound 58]
3-[(3-Nitrophenyl)sulfonylamino]-2-oxochromen-8-yl 3-bromobenzenesulfonate [Compound 59]
2-Oxo-3-[[3-(trifluoromethyl)phenyl]sulfonylamino]-chromen-8-yl 3-bromobenzenesulfonate [Compound 60]
2-Oxo-3-[[4-(trifluoromethyl)phenyl]sulfonylamino]-chromen-8-yl 3-bromobenzenesulfonate [Compound 61]
3-[(3-Nitrophenyl)sulfonylamino]-2-oxochromen-8-yl 4-phenylbenzenesulfonate [Compound 62]
2-Oxo-3-[[3-(trifluoromethyl)phenyl]sulfonylamino]-chromen-8-yl 4-phenylbenzenesulfonate [Compound 63]
2-Oxo-3-[[4-(trifluoromethyl)phenyl]sulfonylamino]-chromen-8-yl 4-phenylbenzenesulfonate [Compound 64]
3-[(3-Bromophenyl)sulfonylamino]-2-oxochromen-8-yl 4-phenylbenzenesulfonate [Compound 65]
2-Oxo-3-[(4-phenylphenyl)sulfonylamino]chromen-8-yl 4-phenylbenzenesulfonate [Compound 66]
2-Oxo-3-[[4-(trifluoromethyl)phenyl]sulfonylamino]-chromen-8-yl 3-nitrobenzenesulfonate [Compound 67]
2-Oxo-3-[[4-(trifluoromethyl)phenyl]sulfonylamino]-chromen-8-yl 3-(trifluoromethyl)benzenesulfonate [Compound 68]
3-[(3-Nitrophenyl)sulfonylamino]-2-oxochromen-8-yl 4-(trifluoromethyl)benzenesulfonate [Compound 69]
2-Oxo-3-[(4-phenylphenyl)sulfonylamino]chromen-8-yl 4-(trifluoromethyl)benzenesulfonate [Compound 70]

TABLE 1

| Compound No. | $R_1$ | $R_2$ |
| --- | --- | --- |
| 1 | 4-OMePh | 4-OMePh |
| 2 | 3-OMePh | 3-OMePh |
| 3 | 2-OMePh | 2-OMePh |
| 4 | 4-MePh | 4-MePh |
| 5 | 3-MePh | 3-MePh |
| 6 | 2-MePh | 2-MePh |
| 7 | 4-ClPh | 4-ClPh |
| 8 | 3-ClPh | 3-ClPh |
| 9 | 2-ClPh | 2-ClPh |
| 10 | 4-FPh | 4-FPh |
| 11 | 3-FPh | 3-FPh |
| 12 | 2-FPh | 2-FPh |
| 13 | 4-CNPh | 4-CNPh |
| 14 | 3-CNPh | 3-CNPh |
| 15 | 2-CNPh | 2-CNPh |
| 16 | 4-NO$_2$Ph | 4-NO$_2$Ph |
| 17 | 3-NO$_2$Ph | 3-NO$_2$Ph |
| 18 | 2-NO$_2$Ph | 2-NO$_2$Ph |
| 19 | 4-OHPh | 4-OHPh |
| 20 | 4-CNPh | Ph |
| 21 | Ph | 4-CNPh |
| 22 | Ph | 3-CNPh |
| 23 | Ph | 4-NO$_2$Ph |
| 24 | Ph | 3-NO$_2$Ph |
| 25 | Ph | 3-FPh |
| 26 | Ph | 3,4-F$_2$Ph |
| 27 | Ph | 4-CF$_3$Ph |
| 28 | Ph | 3-CF$_3$Ph |
| 29 | Ph | 4-ClPh |
| 30 | Ph | 4-PhPh |
| 31 | Ph | 3-BrPh |
| 32 | 3-BrPh | 3-BrPh |
| 33 | 3-CF$_3$Ph | 3-CF$_3$Ph |
| 34 | 3-BrPh | Ph |
| 35 | 3-CF$_3$Ph | Ph |

TABLE 2

| Compound No. | $R_1$ | $R_2$ |
| --- | --- | --- |
| 36 | 3-Py | 3-BrPh |
| 37 | Me | 3-BrPh |
| 38 | 3-BrPh | 3-Py |
| 39 | 3-BrPh | Me |
| 40 | Ph | Me |
| 41 | 4-NO$_2$Ph | 3-CF$_3$Ph |
| 42 | 3-CF$_3$Ph | 4-NO$_2$Ph |
| 43 | 2-thienyl | 3-NO$_2$Ph |
| 44 | 3-NO$_2$Ph | 2-thienyl |
| 45 | 3-NO$_2$Ph | 4-COOHPh |
| 46 | 4-NH$_2$Ph | 3-CF$_3$Ph |
| 47 | 3-CF$_3$Ph | 4-NH$_2$Ph |
| 48 | 4-COOEtPh | 3-NO$_2$Ph |
| 49 | 4-COOHPh | 3-NO$_2$Ph |
| 50 | 3-NO$_2$Ph | 3-CF$_3$Ph |
| 51 | 3-CF$_3$Ph | 3-NO$_2$Ph |
| 52 | 3-CF$_3$Ph | 4-PhPh |
| 53 | 3-BrPh | 4-PhPh |
| 54 | 3-NO$_2$Ph | 3-BrPh |
| 55 | 3-NO$_2$Ph | 4-PhPh |
| 56 | 3-CF$_3$Ph | 3-BrPh |
| 57 | 4-CF$_3$Ph | 3-CF$_3$Ph |
| 58 | 4-CF$_3$Ph | 3-BrPh |
| 59 | 3-BrPh | 3-NO$_2$Ph |
| 60 | 3-BrPh | 3-CF$_3$Ph |
| 61 | 3-BrPh | 4-CF$_3$Ph |
| 62 | 4-PhPh | 3-NO$_2$Ph |
| 63 | 4-PhPh | 3-CF$_3$Ph |
| 64 | 4-PhPh | 4-CF$_3$Ph |
| 65 | 4-PhPh | 3-BrPh |
| 66 | 4-PhPh | 4-PhPh |
| 67 | 3-NO$_2$Ph | 4-CF$_3$Ph |
| 68 | 3-CF$_3$Ph | 4-CF$_3$Ph |
| 69 | 4-CF$_3$Ph | 3-NO$_2$Ph |
| 70 | 4-CF$_3$Ph | 4-PhPh |

As hereunder, preferred embodiments of the present invention will be shown.

(1) A preventive or therapeutic agent for inflammatory disease or degenerative intervertebral disk disease containing at least one member of a coumarin derivative represented by the above formula (I), and a pharmaceutically acceptable salt and hydrate thereof.

(2) The preventive or therapeutic agent according to the above (1), wherein $R_1$ and $R_2$ are the same or different, and are phenyl which may be substituted with alkoxy, alkyl, cyano, nitro, hydroxy, trifluoromethyl, amino, carboxy, alkoxycarbonyl, phenyl or one or two halogen(s).

(3) The preventive or therapeutic agent according to the above (2), wherein $R_1$ and $R_2$ are the same or different, and are phenyl which is substituted with alkoxy, alkyl, cyano, nitro, hydroxy, trifluoromethyl, amino, carboxy, alkoxycarbonyl, phenyl or one or two halogen(s).

(4) The preventive or therapeutic agent according to the above (3), wherein both of $R_1$ and $R_2$ are phenyl which is substituted with trifluoromethyl.

(5) The preventive or therapeutic agent according to the above (3), wherein one of $R_1$ and $R_2$ is phenyl which is substituted with trifluoromethyl.

(6) The preventive or therapeutic agent according to the above (5), wherein one of $R_1$ and $R_2$ is phenyl which is substituted with trifluoromethyl and the other is phenyl which is substituted with halogen.

(7) The preventive or therapeutic agent according to the above (6), wherein the halogen is bromine.

(8) The preventive or therapeutic agent according to any of the above (1) to (7), wherein the inflammatory disease is chronic obstructive pulmonary disease or pulmonary fibrosis.

(9) The preventive or therapeutic agent according to any of the above (1) to (8), wherein the agent is an agent for oral administration.

(10) The preventive or therapeutic agent according to any of the above (1) to (8), wherein the agent is an agent for injection.

(11) The preventive or therapeutic agent according to any of the above (1) to (8), wherein the agent is an agent for external application.

(12) The preventive or therapeutic agent according to the above (11), wherein the agent is an inhalant.

(13) The preventive or therapeutic agent according to the above (12), wherein the agent is an agent for transpulmonary administration.

(14) A coumarin derivative represented by the above formula (I), or a pharmaceutically acceptable salt or hydrate thereof for use in the prevention or the treatment of inflammatory disease or degenerative intervertebral disk disease.

(15) The coumarin derivative or a pharmaceutically acceptable salt or hydrate thereof according to the above (14), wherein $R_1$ and $R_2$ are the same or different, and are phenyl which may be substituted with alkoxy, alkyl, cyano, nitro, hydroxy, trifluoromethyl, amino, carboxy, alkoxycarbonyl, phenyl or one or two halogen(s).

(16) The coumarin derivative or a pharmaceutically acceptable salt or hydrate thereof according to the above (15), wherein $R_1$ and $R_2$ are the same or different, and are phenyl which is substituted with alkoxy, alkyl, cyano, nitro, hydroxy, trifluoromethyl, amino, carboxy, alkoxycarbonyl, phenyl or one or two halogen(s).

(17) The coumarin derivative or a pharmaceutically acceptable salt or hydrate thereof according to the above (16), wherein both of $R_1$ and $R_2$ are phenyl which is substituted with trifluoromethyl.

(18) The coumarin derivative or a pharmaceutically acceptable salt or hydrate thereof according to the above (16), wherein one of $R_1$ and $R_2$ is phenyl which is substituted with trifluoromethyl.

(19) The coumarin derivative or a pharmaceutically acceptable salt or hydrate thereof according to the above (18), wherein one of $R_1$ and $R_2$ is phenyl which is substituted with trifluoromethyl and the other is phenyl which is substituted with halogen.

(20) The coumarin derivative or a pharmaceutically acceptable salt or hydrate thereof according to the above (19), wherein the halogen is bromine.

(21) The coumarin derivative or a pharmaceutically acceptable salt or hydrate thereof according to any of the above (14) to (20), wherein the inflammatory disease is chronic obstructive pulmonary disease or pulmonary fibrosis.

(22) A method for preventing or treating inflammatory disease or degenerative intervertebral disk disease, comprising administering an effective dose of at least one member of a coumarin derivative represented by the above formula (I), and a pharmaceutically acceptable salt and hydrate thereof to a patient suffering from inflammatory disease or degenerative intervertebral disk disease.

(23) The method for preventing or treating according to the above (22), wherein $R_1$ and $R_2$ are the same or different, and are phenyl which may be substituted with alkoxy, alkyl, cyano, nitro, hydroxy, trifluoromethyl, amino, carboxy, alkoxycarbonyl, phenyl or one or two halogen(s).

(24) The method for preventing or treating according to the above (23), wherein $R_1$ and $R_2$ are the same or different, and are phenyl which is substituted with alkoxy, alkyl, cyano, nitro, hydroxy, trifluoromethyl, amino, carboxy, alkoxycarbonyl, phenyl or one or two halogen(s).

(25) The method for preventing or treating according to the above (24), wherein both of $R_1$ and $R_2$ are phenyl which is substituted with trifluoromethyl.

(26) The method for preventing or treating according to the above (24), wherein one of $R_1$ and $R_2$ is phenyl which is substituted with trifluoromethyl.

(27) The method for preventing or treating according to the above (26), wherein one of $R_1$ and $R_2$ is phenyl which is substituted with trifluoromethyl and the other is phenyl which is substituted with halogen.

(28) The method for preventing or treating according to the above (27), wherein the halogen is bromine.

(29) The method for preventing or treating according to any of the above (22) to (28), wherein the inflammatory disease is chronic obstructive pulmonary disease or pulmonary fibrosis.

(30) Use of a coumarin derivative represented by the above formula (1) or a pharmaceutically acceptable salt or hydrate thereof in the manufacture of a drug for the prevention or the treatment of inflammatory disease or degenerative intervertebral disk disease.

(31) The use according to the above (30), wherein $R_1$ and $R_2$ are the same or different, and are phenyl which may be substituted with alkoxy, alkyl, cyano, nitro, hydroxy, trifluoromethyl, amino, carboxy, alkoxycarbonyl, phenyl or one or two halogen(s).

(32) The use according to the above (31), wherein $R_1$ and $R_2$ are the same or different, and are phenyl which is substituted with alkoxy, alkyl, cyano, nitro, hydroxy, trifluoromethyl, amino, carboxy, alkoxycarbonyl, phenyl or one or two halogen(s).

(33) The use according to the above (32), wherein both of $R_1$ and $R_2$ are phenyl which is substituted with trifluoromethyl.

(34) The use according to the above (32), wherein one of $R_1$ and $R_2$ is phenyl which is substituted with trifluoromethyl.

(35) The use according to the above (34), wherein one of $R_1$ and $R_2$ is phenyl which is substituted with trifluoromethyl and the other is phenyl which is substituted with halogen.

(36) The use according to the above (35), wherein the halogen is bromine.

(37) The use according to any of the above (30) to (36), wherein the inflammatory disease is chronic obstructive pulmonary disease or pulmonary fibrosis.

The present compound may be made into a pharmaceutical composition where various additives for drugs such as filler, binder, moisturizer, disintegrating agent, lubricant or diluent suitable for the dosage form are combined therewith depending upon the necessity. As to an agent for oral administration, it may be made into a dosage form such as tablet, capsule, diluted powder, granule, liquid, syrup or sublingual preparation. As to a parenteral agent, it may be made into an agent for injection and an agent for external application, etc. for subcutaneous, intramuscular, intra-articular or intravenous administration. As to an agent for external application, it may be made into inhalant, etc. for administration via lung or into nasal cavity in addition to ointment, cream, lotion, plaster, aerosol and suppository. In the prescription, the present compound may be used in its pharmaceutically acceptable salt or hydrate and it may be used solely or by means of appropriate combination. Alternatively, it may be made into a compounded agent with other pharmaceutically active ingredient.

With regard to the additive in preparing an oral agent, it is possible to appropriately combine commonly used excipient (such as lactose, mannitol, corn starch or potato starch), binder (such as crystalline cellulose, cellulose derivative, gum arabic, corn starch or gelatin), disintegrant (such as corn starch, potato starch or carboxymethyl cellulose potassium), lubricant (such as talc or magnesium stearate) and others (such as extender, moisturizer, buffer, preservative or fragrance) and it is also possible to add corrigent, aromatizing agent, etc. thereto.

When preparation is conducted as a liquid agent or as an emulsified, suspended or viscous injection agent, it is also possible to appropriately add commonly used solubilizing agent, suspending agent, emulsifier, stabilizer, preservative, isotonic agent, thickening agent, base for intraarticular administration, etc. and, usually, a sterilizing treatment is carried out.

Although the preferred dose of the present compound may vary depending upon the subject to be administered (age, body weight, etc. of a patient), type and extent of the disease, dosage form, administering method, administering period, etc., it is usual that 0.5 to 1000 mg or, preferably, 1 to 500 mg of the present compound is orally administered to an adult once daily or by dividing into several times a day. In the case of parenteral administration, the daily dose is made into a level of from one-third to one-tenth of each of the above-mentioned doses and, usually, it may be administered once daily or by dividing into several times a day. In the case of a sustained-release preparation where a drug is released for a very long period, it is preferred to administer about once a week to once a year.

EXAMPLES

The present invention will now be specifically illustrated hereunder by Examples but the present invention is not limited thereto at all.

The melting point as the physical property of the present compound prepared by the following Examples 1 to 5 was measured using a melting point measuring device of a Yamato MP-21 type and no correction was conducted for a thermometer. NMR spectrum was measured using a nuclear magnetic resonance device of a Brucker Avance III 500 type using tetramethylsilane as an internal standard. Silica gel column chromatography was conducted using PSQ 100 B (manufactured by Fuji Silysia Chemical). Thin layer chromatography was conducted using Silica Gel F254 (Merck No. 5715) and, for the detection, UV lamp was used together with a coloring reagent of a 5 w/v % ethanolic solution of phosphomolybdic acid and iodine-silica gel. With regard to reagents and solvents, the commercially available ones were used just they were.

Example 1

(1) Production of 3-acetylamino-2-oxochromen-8-yl benzenesulfonate

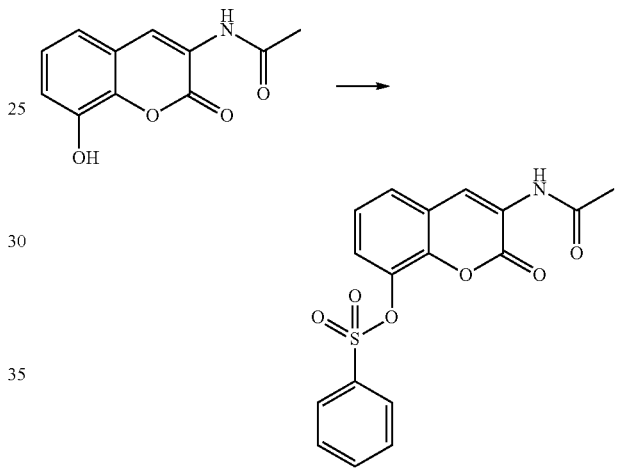

Benzenesulfonyl chloride (4.0 g, 22.8 mmol) was added to a solution of 3-acetylamino-2-oxo-8-hydroxychromen (5.0 g, 22.8 mmol) in pyridine (50 mL) followed by stirring for one night. Chloroform (100 mL) was added thereto and crystals were filtered therefrom and washed with hexane. The crystals were dried to give 7.0 g (85%) of the title compound.

Mp. 229-231° C. $^1$H-NMR (DMSO-$d_6$) δ: 2.15 (s, 3H), 7.22-7.34 (m, 2H), 7.58-7.89 (m, 6H), 8.58 (s, 1H), 9.81 (s, 1H).

(2) Production of 3-amino-2-oxochromen-8-yl benzenesulfonate

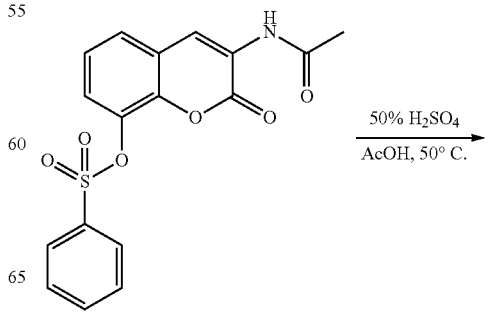

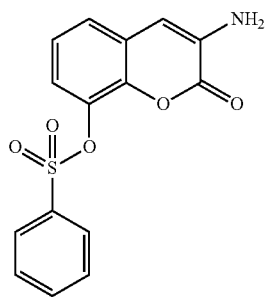

To a solution of the compound produced in the above (1) (3.0 g, 8.3 mmol) in acetic acid (30 mL) was added 50 vol % sulfuric acid (30 mL) followed by stirring at 50° C. After the crystals were completely dissolved, the reaction mixture was allowed to cool and added to water. The crystals separated out therefrom were filtered and dried to give 2.2 g (83%) of the title compound.

Mp. 129-131° C. $^1$HNMR (DMSO-$d_6$) δ: 5.88 (s, 2H), 6.64 (s, 1H), 6.93-7.87 (m, 8H).

(3) Production of 3-[(4-nitrophenyl)sulfonylamino]-2-oxochromen-8-yl benzenesulfonate [Compound 23]

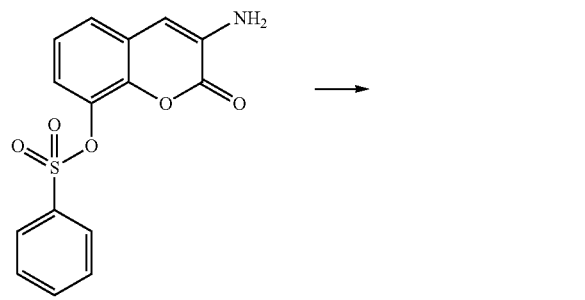

To a solution of the compound produced in the above (2) (1 g, 3.2 mmol) in pyridine (10 mL) was added 4-nitrobenzenesulfonyl chloride (1.0 g, 4.8 mmol) followed by stirring at room temperature for one night. After the solvent was evaporated therefrom in vacuo, the residue was purified by silica gel column chromatography (hexane:ethyl acetate=3:2 and then 100% chloroform). The resulting crude crystals were recrystallized from chloroform to give 0.8 g (52%) of the compound 23.

Example 2

Production of 3-[(4-methoxyphenyl)sulfonylamino]-2-oxochromen-8-yl 4-methoxybenzenesulfonate [Compound 1]

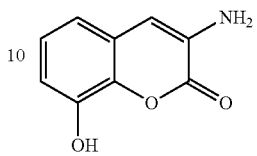

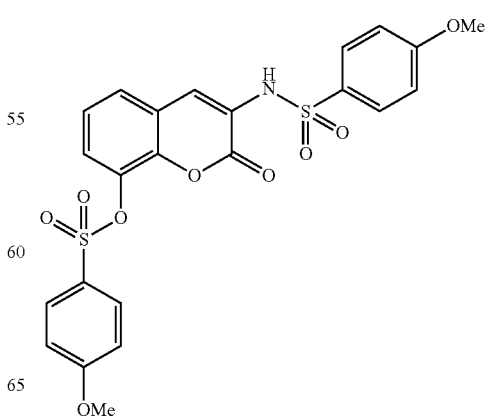

3-Amino-2-oxo-8-hydroxychromen (500 mg, 2.8 mmol) was suspended in methylene chloride (20 mL), pyridine (1.4 mL, 17 mmol) was dropped thereinto under cooling with ice, then 4-methoxybenzenesulfonyl chloride (3.5 g, 17 mmol) was added thereto under cooling with ice and the mixture was stirred at room temperature for 15 hours. The reaction solution was washed with water and a saturated saline solution and the organic layer was dried over sodium sulfate. The solvent was evaporated therefrom in vacuo and the resulting residue was purified by silica gel column chromatography (chloroform:methanol=120:1) to give 980 mg (67%) of the compound 1 as a solid.

Example 3

Production of 3-[(4-hydroxyphenyl)sulfonylamino]-2-oxochromen-8-yl 4-hydroxybenzenesulfonate [Compound 19]

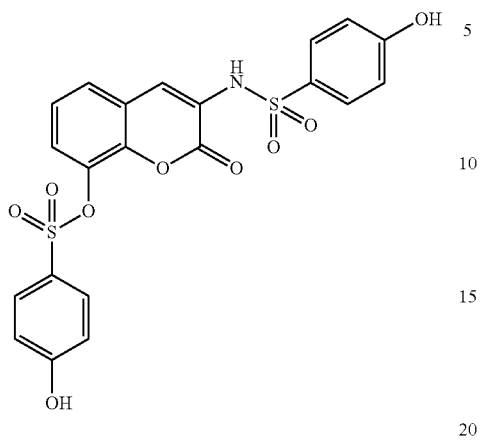

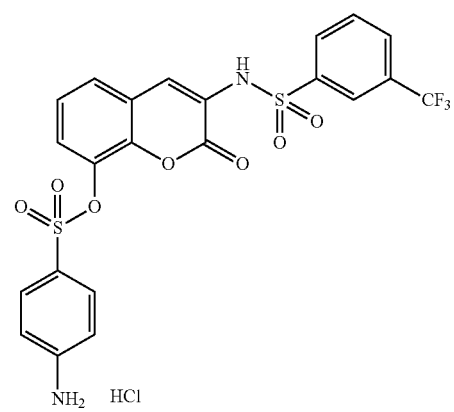

The compound 1 (300 mg, 0.6 mmol) was dissolved in anhydrous methylene chloride (1.8 mL), substitution with argon was conducted and the mixture was cooled down to −78° C. Boron tribromide (3.8 mL, 3.8 mmol) was dropped into the reaction solution followed by stirring at room temperature for 20 hours. Ice water was added to the reaction solution and the solid separated out therefrom were filtered and dried in vacuo over diphosphorus pentaoxide. This solid was purified by silica gel column chromatography (chloroform:methanol=95:5) to give 40 mg (14%) of the compound 19 as a solid.

Example 4

Production of 2-oxo-3-[[3-(trifluoromethyl)phenyl]-sulfonylamino]chromen-8-yl 4-aminobenzenesulfonate [Compound 46]

5% Pd—C (10 mg) was added to a solution of the compound 41 (0.2 g, 0.4 mmol) produced by the same method as in Example 1 in chloroform (10 mL) followed by stirring in a hydrogen atmosphere for 2 hours. After filtering off the catalyst, the solvent was evaporated therefrom in vacuo and a hydrogen chloride-dioxane solution (0.2 mL, 0.8 mmol) was added to the residue. The solvent was evaporated in vacuo and the crystals separated out therefrom were filtered and dried to give 30 mg (15%) of the compound 46.

Example 5

Production of 4-[3-[(3-nitrophenyl)sulfonylamino]-2-oxochromen-8-yl] oxysulfonylbenzoic acid [Compound 49]

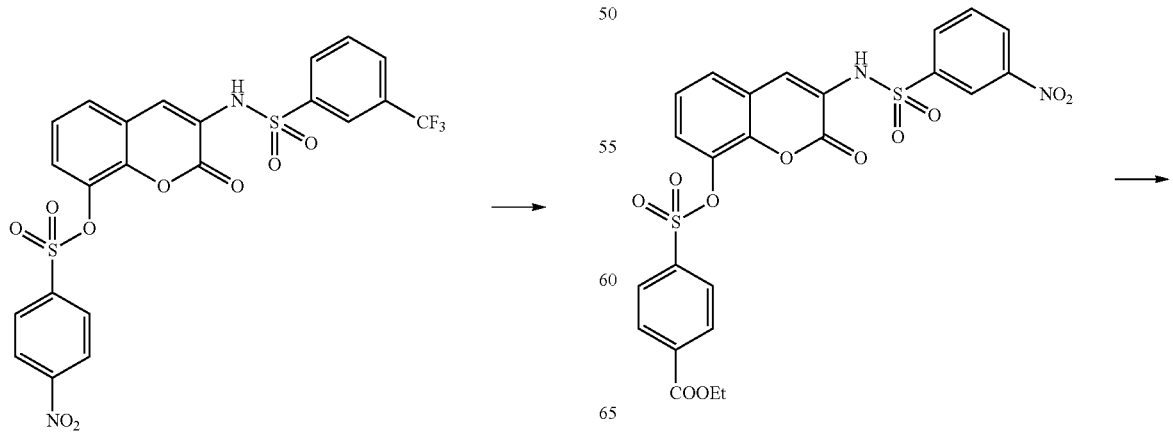

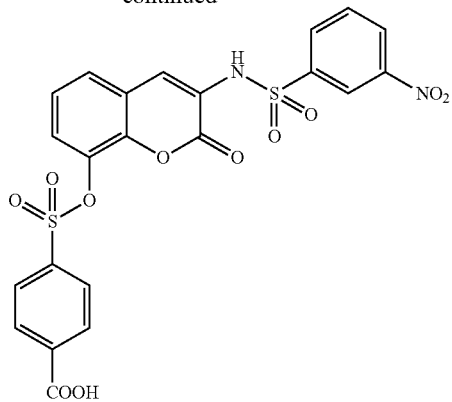

To a solution of the compound 48 (0.1 g, 0.2 mmol) produced by the same method as in Example 1 in methanol (5 mL) was added a 10 mol/L aqueous solution of sodium hydroxide (0.2 mL, 2 mmol as NaOH) followed by stirring at room temperature for 0.5 hour. The solvent was evaporated therefrom in vacuo, water (5 mL) was added to the residue and the mixture was extracted with chloroform. The solvent was evaporated in vacuo and the residue was crystallized from petroleum ether-ether to give 20 mg (22%) of the compound 49.

With regard to compounds other than the above-mentioned ones, they were produced using appropriate starting materials whereupon the compounds 2 to 18, 32 and 33 were produced by the same method as in Example 2, the compound 47 was produced by the same method as in Example 4 and other compounds were produced by the same method as in Example 1.

Physical property data of the compounds produced in the above Examples are shown in Tables 3 to 9.

TABLE 3

| Compound No. | Physical Property |
|---|---|
| Compound 1 | Mp. 161-162° C. $^1$H-NMR (DMSO-$d_6$) δ: 3.82 (s, 3H), 3.83 (s 3H), 7.08-7.11 (m, 4H), 7.18-7.20 (m, 1H), 7.30-7.33 (m, 1H), 7.75-7.86 (m, 4H), 7.87-7.88 (m, 2H), 10.28 (s, 1H). |
| Compound 2 | Mp. 125-126° C. $^1$H-NMR (DMSO-$d_6$) δ: 3.78 (s, 3H), 3.82 (s, 3H), 7.25-7.34 (m, 6H), 7.42-7.52 (m, 4H), 7.73-7.75 (m, 1H), 7.81 (s, 1H), 10.46 (s, 1H). |
| Compound 3 | Mp. 130-131° C. $^1$H-NMR (DMSO-$d_6$) δ: 3.72 (s, 3H), 3.87 (s, 3H), 7.01-7.04 (m, 1H), 7.06-7.09 (m, 1H), 7.22-7.31 (m, 4H), 7.63-7.71 (m, 3H), 7.72-7.74 (m, 1H), 7.78-7.80 (m, 2H), 9.69 (s, 1H). |
| Compound 4 | Mp. 180-181° C. $^1$H-NMR (DMSO-$d_6$) δ: 2.36 (s, 3H), 2.37 (s, 3H), 7.19-7.21 (m, 1H), 7.30-7.33 (m, 1H), 7.39-7.41 (m, 4H), 7.70-7.72 (m, 3H), 7.77 (s, 1H), 7.81-7.83 (m, 2H), 10.37 (s, 1H). |
| Compound 5 | Mp. 125-126° C. $^1$H-NMR (DMSO-$d_6$) δ: 2.31 (s, 3H), 2.39 (s, 3H), 7.25-7.27 (m, 1H), 7.31-7.33 (m, 1H), 7.41-7.42 (m, 1H), 7.48-7.55 (m, 4H), 7.70-7.73 (m, 3H), 7.77-7.78 (m, 2H), 10.41 (s, 1H). |
| Compound 6 | Mp. 75-76° C. $^1$H-NMR (DMSO-$d_6$) δ: 2.62 (s, 3H), 2.72 (s, 3H), 7.20-7.50 (m, 6H), 7.55-7.65 (m, 4H), 7.66-7.87 (m, 2H), 10.55 (s, 1H). |
| Compound 7 | Mp. 200-201° C. $^1$H-NMR (DMSO-$d_6$) δ: 7.30-7.35 (m, 2H), 7.66-7.74 (m, 5H), 7.85-7.87 (m, 3H), 7.91-7.92 (m, 2H), 10.55 (s, 1H). |
| Compound 8 | Mp. 105-106° C. $^1$H-NMR (DMSO-$d_6$) δ: 7.36-7.37 (m, 2H), 7.58-7.65 (m, 2H), 7.76-7.81 (m, 4H), 7.86-7.89 (m, 3H), 7.98-7.99 (m, 1H), 10.60 (s, 1H). |

TABLE 3-continued

| Compound No. | Physical Property |
|---|---|
| Compound 9 | Mp. 180-181° C. $^1$H-NMR (DMSO-$d_6$) δ: 7.21-7.23 (m, 1H), 7.29-7.32 (m, 1H), 7.50-7.55 (m, 2H), 7.68-7.70 (m, 3H), 7.78-7.82 (m, 3H), 7.87-7.89 (m, 1H), 8.02-8.04 (m, 1H), 10.58 (s, 1H). |
| Compound 10 | Mp. 195-196° C. $^1$H-NMR (DMSO-$d_6$) δ: 7.29-7.35 (m, 2H), 7.41-7.45 (m, 4H), 7.74-7.75 (m, 1H), 7.83 (s, 1H), 7.90-7.93 (m, 2H), 7.96-7.99 (m, 2H), 10.46 (s, 1H). |

TABLE 4

| Compound No. | Physical Property |
|---|---|
| Compound 11 | Mp. 150-151° C. $^1$H-NMR (DMSO-$d_6$) δ: 7.32-7.38 (m, 2H), 7.56-7.69 (m, 5H), 7.75-7.78 (m, 4H), 7.86 (s, 1H), 10.58 (s, 1H). |
| Compound 12 | Mp. 200-201° C. $^1$H-NMR (DMSO-$d_6$) δ: 7.33-7.40 (m, 4H), 7.45-7.53 (m, 2H), 7.71-7.76 (m, 3H), 7.82-7.85 (m, 3H), 10.65 (s, 1H). |
| Compound 13 | Mp. 130-131° C. $^1$H-NMR (DMSO-$d_6$) δ: 7.25-7.45 (m, 2H), 7.76 (s, 1H), 7.87 (s, 1H), 7.95-8.20 (m, 8H), 10.74 (s, 1H). |
| Compound 14 | Mp. 205-206° C. $^1$H-NMR (DMSO-$d_6$) δ: 7.37 (s, 2H), 7.38-7.84 (m, 4H), 8.10-8.12 (m, 1H), 8.17-8.23 (m, 3H), 8.39 (s, 1H), 8.46 (s, 1H), 10.67 (s, 1H). |
| Compound 15 | Mp. 225-226° C. $^1$H-NMR (DMSO-$d_6$) δ: 7.36-7.39 (m, 1H), 7.42-7.44 (m, 1H), 7.72-7.74 (m, 1H), 7.85-7.95 (m, 5H), 7.97-7.99 (m, 1H), 8.05-8.06 (m, 1H), 8.09-8.10 (m, 1H), 8.18-8.20 (m, 1H), 10.85 (s, 1H). |
| Compound 16 | Mp. 230-231° C. $^1$H-NMR (DMSO-$d_6$) δ: 7.36-7.38 (m, 2H), 7.76-7.77 (m, 1H), 7.87-7.88 (m, 1H), 8.12-8.16 (m, 4H), 8.36-8.41 (m, 4H), 10.80 (s, 1H). |
| Compound 17 | Mp. 175-176° C. $^1$H-NMR (DMSO-$d_6$) δ: 7.36-7.39 (m, 1H), 7.43-7.45 (m, 1H), 7.77-7.79 (m, 1H), 7.83-7.86 (m, 1H), 7.88-7.91 (m, 2H), 8.20-8.22 (m, 1H), 8.29-8.31 (m, 1H), 8.49-8.52 (m, 3H), 8.65 (s, 1H), 10.75 (s, 1H). |
| Compound 18 | Mp. 180-181° C. $^1$H-NMR (DMSO-$d_6$) δ: 7.37-7.39 (m, 2H), 7.76 (s, 1H), 7.81-7.85 (m, 1H), 7.85-7.90 (m, 3H), 7.98-8.03 (m, 3H), 8.08-8.10 (m, 1H), 8.16-8.18 (m, 1H), 10.75 (s, 1H). |
| Compound 19 | Mp. 215-216° C. $^1$H-NMR (DMSO-$d_6$) δ: 6.86-7.13 (m, 6H), 7.38-7.40 (m, 1H), 7.67-7.68 (m, 1H), 7.71-7.77 (m, 4H), 10.17 (s, 1H), 10.38-10.56 (m, 2H). |
| Compound 20 | Mp. 227-228° C. $^1$H-NMR (DMSO-$d_6$) δ: 7.33-7.35 (m, 2H), 7.59-7.62 (m, 2H), 7.68-7.69 (m, 1H), 7.76-7.77 (m, 1H), 7.82 (s, 1H), 7.91-7.93 (m, 2H), 8.04-8.10 (m, 4H), 10.49 (s, 1H). |

TABLE 5

| Compound No. | Physical Property |
|---|---|
| Compound 21 | Mp. 89-90° C. $^1$H-NMR (DMSO-$d_6$) δ: 7.57-7.60 (m, 2H), 7.72-7.73 (m, 2H), 7.82-7.84 (m, 3H), 8.06-8.11 (m, 6H), 10.73 (s, 1H). |
| Compound 22 | Mp. 86-89° C. $^1$H-NMR (DMSO-$d_6$) δ: 7.59-7.61 (m, 2H), 7.74-7.76 (m, 2H), 7.78-7.80 (m, 3H), 8.12-8.16 (m, 6H), 10.69 (s, 1H). |
| Compound 23 | Mp. 154-155° C. $^1$H-NMR (DMSO-$d_6$) δ: 7.27-8.42 (m, 14H), 10.81 (brs, 1H). |
| Compound 24 | Mp. 116-117° C. $^1$H-NMR (DMSO-$d_6$) δ: 7.26-8.68 (m, 13H), 10.79 (brs, 1H). |
| Compound 25 | Mp. 130-132° C. $^1$H-NMR (DMSO-$d_6$) δ: 7.26-7.84 (m, 13H), 10.56 (brs, 1H). |
| Compound 26 | Mp. 157-159° C. $^1$H-NMR (DMSO-$d_6$) δ: 7.27-8.06 (m, 12H), 10.57 (brs, 1H). |
| Compound 27 | Mp. 173-175° C. $^1$H-NMR (DMSO-$d_6$) δ: 7.28-8.13 (m, 13H), 10.70 (brs, 1H). |
| Compound 28 | Mp. 157-159° C. $^1$H-NMR (DMSO-$d_6$) δ: 7.27-8.26 (m, 13H), 10.66 (brs, 1H). |

TABLE 5-continued

| Compound No. | Physical Property |
|---|---|
| Compound 29 | Mp. 140-142° C. $^1$H-NMR (DMSO-$d_6$) δ: 7.27-7.91 (m, 13H), 10.53 (brs, 1H). |
| Compound 30 | Mp. 166-168° C. $^1$H-NMR (DMSO-$d_6$) δ: 7.25-8.01 (m, 18H), 10.50 (brs, 1H). |
| Compound 31 | Mp. 165-167° C. $^1$H-NMR (DMSO-$d_6$) δ: 7.28-8.11 (m, 13H), 10.57 (brs, 1H). |
| Compound 32 | Mp. 139-140° C. $^1$H-NMR (DMSO-$d_6$) δ: 7.35-8.12 (m, 12H), 10.61 (brs, 1H). |
| Compound 33 | Mp. 136-138° C. $^1$H-NMR (DMSO-$d_6$) δ: 7.37-8.26 (m, 12H), 10.67 (brs, 1H). |
| Compound 34 | Mp. 121-124° C. $^1$H-NMR (DMSO-$d_6$) δ: 7.32-7.98 (m, 13H), 10.49 (brs, 1H). |
| Compound 35 | Mp. 127-129° C. $^1$H-NMR (DMSO-$d_6$) δ: 7.35-8.12 (m, 13H), 10.47 (brs, 1H). |
| Compound 36 | Mp. 149-151° C. $^1$H-NMR (DMSO-$d_6$) δ: 7.37-8.97 (m, 12H), 10.59 (brs, 1H). |

TABLE 6

| Compound No. | Physical Property |
|---|---|
| Compound 37 | Mp. 151-153° C. $^1$H-NMR (DMSO-$d_6$) δ: 3.49 (s, 3H), 7.38-8.16 (m, 8H), 10.64 (brs, 1H). |
| Compound 38 | Mp. 181-183° C. $^1$H-NMR (DMSO-$d_6$) δ: 7.35-9.06 (m, 11H), 10.70 (brs, 1H). |
| Compound 39 | Mp. 150-152° C. $^1$H-NMR (DMSO-$d_6$) δ: 3.17 (s, 3H), 7.33-8.05 (m, 8H), 9.74 (brs, 1H). |
| Compound 40 | Mp. 161-163° C. $^1$H-NMR (DMSO-$d_6$) δ: 3.16 (s, 3H), 7.25-7.90 (m, 9H), 9.70 (s, 1H). |
| Compound 41 | Mp. 186-188° C. $^1$H-NMR (DMSO-$d_6$) δ: 7.35-8.41 (m, 12H), 10.65 (brs, 1H). |
| Compound 42 | Mp. 101-103° C. $^1$H-NMR (DMSO-$d_6$) δ: 7.37-8.42 (m, 12H), 10.81 (brs, 1H). |
| Compound 43 | Mp. 155-157° C. $^1$H-NMR (DMSO-$d_6$) δ: 7.16-8.69 (m, 11H), 10.82 (brs, 1H). |
| Compound 44 | Mp. 138-141° C. $^1$H-NMR (DMSO-$d_6$) δ: 7.18-8.57 (m, 11H), 10.64 (brs, 1H). |
| Compound 45 | Mp. 127° C. (dec.). $^1$H-NMR (DMSO-$d_6$) δ: 7.39-8.67 (m, 12H), 9.76 (s, 1H). |
| Compound 46 | Mp. 114° C. (dec.). $^1$H-NMR (DMSO-$d_6$) δ: 6.57-8.27 (m, 15H), 10.67 (brs, 1H). |
| Compound 47 | Mp. 136-138° C. $^1$H-NMR (DMSO-$d_6$) δ: 6.12 (brs, 2H), 6.57-8.13 (m, 12H), 9.92 (s, 1H). |
| Compound 48 | Mp. 153-154° C. $^1$H-NMR (DMSO-$d_6$) δ: 1.34 (t, J = 6.5 Hz, 3H), 4.36 (q, J = 6.5 Hz, 2H), 7.25-8.68 (m, 12H), 10.79 (brs, 1H). |
| Compound 49 | Mp. 168-170° C. $^1$H-NMR (DMSO-$d_6$) δ: 7.24-7.35 (m, 2H), 7.79-8.71 (m, 10H), 10.79 (brs, 1H). |
| Compound 50 | Mp. 166-167° C. $^1$H NMR (DMSO-$d_6$) δ: 7.39 (dd, J = 8.0, 8.0 Hz, 1 H), 7.43-7.45 (m, 1 H), 7.80 (dd, J = 8.0, 1.5 Hz, 1 H), 7.83-7.87 (m, 2 H), 7.90 (s, 1 H), 8.10 (d, J = 8.0 Hz, 1 H), 8.19 (d, J = 8.0 Hz, 1 H), 8.21-8.23 (m, 1 H), 8.25 (s, 1 H), 8.51-8.55 (m, 2 H), 10.65 (brs, 1 H). |

TABLE 7

| Compound No. | Physical Property |
|---|---|
| Compound 51 | Mp. 170-171° C. $^1$H NMR (DMSO-$d_6$) δ: 7.36-7.42 (m, 2 H), 7.77-7.78 (m, 1 H), 7.83 (dd, J = 8.0, 8.0 Hz, 1 H), 7.87-7.91 (m, 2 H), 8.02 (s, 1 H), 8.10 (d, J = 8.0 Hz, 1 H), 8.14 (d, J = 8.0 Hz, 1 H), 8.31-8.33 (m, 1 H), 8.51-8.53 (m, 1 H), 8.68-8.69 (m, 1 H), 10.79 (brs, 1 H). |
| Compound 52 | Mp. 153-154° C. $^1$H NMR (DMSO-$d_6$) δ: 7.36-7.40 (m, 2 H), 7.44 (dd, J = 7.4, 7.4 Hz, 1 H), 7.50 (dd, J = 7.7, 7.7 Hz, 1 H), 7.75 (d, J = 7.5 Hz, 2 H), 7.78-7.83 (m, 2 H), 7.85 (s, 1 H), 7.90-7.92 (m, 2 H), 8.00-8.02 (m, 2 H), 8.05-8.07 (m, 2 H), 8.13 (d, J = 8.0 Hz, 1 H), 10.51 (brs, 1 H) |
| Compound 53 | Mp. 146-147° C. $^1$H NMR (DMSO-$d_6$) δ: 7.32-7.38 (m, 2 H), 7.43-7.46 (m, 1 H), 7.48-7.52 (m, 3 H), 7.74-7.81 (m, 4 H), 7.86-7.92 (m, 4 H), 7.96 (dd, J = 6.9, 6.9 Hz, 1 H), 8.01 (d, J = 8.6 Hz, 2 H), 10.54 (brs, 1 H) |
| Compound 54 | Mp. 172-173° C. $^1$H NMR (DMSO-$d_6$) δ: 7.49 (dd, J = 8.0, 8.0 Hz, 1 H), 7.54-7.56 (m, 1 H), 7.68 (dd, J = 8.0, 8.0 Hz, 1 H), 7.80-7.83 (m, 1 H), 7.86-7.89 (m, 2 H), 7.91-7.95 (m, 2 H), 8.12 (m, 1 H), 8.23-8.25 (m, 1 H), 8.55-8.59 (m, 2 H), 10.59 (brs, 1 H) |
| Compound 55 | Mp. 204-205° C. $^1$H NMR (DMSO-$d_6$) δ: 7.37 (dd, J = 8.0, 8.0 Hz, 1 H), 7.41-7.46 (m, 2 H), 7.50-7.53 (m, 2 H), 7.76-7.84 (m, 5 H), 7.90-7.92 (m, 2 H), 7.98-8.00 (m, 2 H), 8.17-8.20 (m, 1 H), 8.46-8.48 (m, 1 H), 8.55-8.56 (m, 1 H), 10.51 (brs, 1 H) |
| Compound 56 | Mp. 158-159° C. $^1$H NMR (DMSO-$d_6$) δ: 7.36-7.44 (m, 2 H), 7.55 (dd, J = 8.0, 8.0 Hz, 1 H), 7.77-7.79 (m, 1 H), 7.82-7.85 (m, 2 H), 7.90-7.93 (m, 2 H), 8.04 (s, 1 H), 8.09-8.11 (m, 2 H), 8.13 (d, J = 8.0 Hz, 1 H), 10.57 (brs, 1 H) |
| Compound 57 | Mp. 140-141° C. $^1$H NMR (DMSO-$d_6$) δ: 7.35-7.39 (m, 2 H), 7.78 (dd, J = 6.6, 2.8 Hz, 1 H), 7.85 (dd, J = 7.9, 7.9 Hz, 1 H), 7.89 (s, 1 H), 7.98 (d, J = 8.4 Hz, 2 H), 8.07-8.10 (m, 3 H), 8.21 (d, J = 8.0 Hz, 1 H), 8.25 (s, 1 H), 10.66 (brs, 1 H). |

TABLE 8

| Compound No. | Physical Property |
|---|---|
| Compound 58 | Mp. 151-152° C. $^1$H NMR (DMSO-$d_6$) δ: 7.33-7.39 (m, 2 H), 7.54 (dd, J = 8.0, 8.0 Hz, 1 H), 7.78 (dd, J = 7.4, 2.0 Hz, 1 H), 7.84 (s, 1 H), 7.89-7.93 (m, 2 H), 8.00 (d, J = 8.4 Hz, 2 H), 8.10-8.12 (m, 3 H), 10.58 (brs, 1 H). |
| Compound 59 | Mp. 163-164° C. $^1$H NMR (DMSO-$d_6$) δ: 7.35-7.40 (m, 2 H), 7.53 (dd, J = 8.0, 8.0 Hz, 1 H), 7.78 (dd, J = 7.1, 2.3 Hz, 1 H), 7.81-7.83 (m, 1 H), 7.90-7.95 (m, 3 H), 7.97 (dd, J = 1.9, 1.9 Hz, 1 H), 8.33-8.35 (m, 1 H), 8.52-8.54 (m, 1 H), 8.70 (dd, J = 1.9, 1.9 Hz, 1 H), 10.83 (brs, 1 H). |
| Compound 60 | Mp. 135-136° C. $^1$H NMR (DMSO-$d_6$) δ: 7.35-7.40 (m, 2 H), 7.52 (dd, J = 8.0, 8.0 Hz, 1 H), 7.79 (dd, J = 7.3, 2.1 Hz, 1 H), 7.81-7.83 (m, 1 H), 7.86 (dd, J = 7.9, 7.9 Hz, 1 H), 7.91-7.93 (m, 2 H), 7.96 (dd, J = 1.8, 1.8 Hz, 1 H), 8.10 (d, J = 7.8 Hz, 1 H), 8.22 (d, J = 8.1 Hz, 1 H), 8.27 (s, 1 H), 10.69 (brs, 1 H). |
| Compound 61 | Mp. 176-177° C. $^1$H NMR (DMSO-$d_6$) δ: 7.40-7.45 (m, 2 H), 7.58 (dd, J = 8.0, 8.0 Hz, 1 H), 7.83 (dd, J = 6.6, 2.6 Hz, 1 H), 7.87 (d, J = 8.0 Hz, 1 H), 7.95-7.98 (m, 2 H), 8.02 (s, 1 H), 8.06 (d, J = 8.4 Hz, 2 H), 8.19 (d, J = 8.2 Hz, 2 H), 10.79 (brs, 1 H). |
| Compound 62 | Mp. 192-193° C. $^1$H NMR (DMSO-$d_6$) δ: 7.30-7.38 (m, 2 H), 7.47-7.55 (m, 3 H), 7.70-7.72 (m, 2 H), 7.75 (dd, J = 7.8, 1.5 Hz, 1 H), 7.83 (dd, J = 8.0, 8.0 Hz, 1 H), 7.88-7.94 (m, 5 H), 8.29-8.31 (m, 1 H), 8.43-8.46 (m, 1 H), 8.66 (dd, J = 1.9, 1.9 Hz, 1 H), 10.90 (brs, 1 H) |
| Compound 63 | Mp. 170-171° C. $^1$H NMR (DMSO-$d_6$) δ: 7.37 (dd, J = 8.2, 1.6 Hz, 1 H), 7.42 (dd, J = 8.0, 8.0 Hz, 1 H), 7.53-7.61 (m, 3 H), 7.76-7.78 (m, 2 H), 7.81-7.85 (m, 2 H), 7.95-8.00 (m, 5 H), 8.08 (d, J = 7.9 Hz, 1 H), 8.24 (d, J = 8.0 Hz, 1 H), 8.30 (s, 1 H), 10.71 (brs, 1 H) |
| Compound 64 | Mp. 196-197° C. $^1$H NMR (DMSO-$d_6$) δ: 7.29-7.36 (m, 2 H), 7.46-7.54 (m, 3 H), 7.69-7.74 (m, 3 H), 7.83-7.92 (m, 7 H), 8.08 (d, J = 8.2 Hz, 2 H), 10.70 (brs, 1 H) |

TABLE 9

| Compound No. | Physical Property |
|---|---|
| Compound 65 | Mp. 182-183° C. $^1$H NMR (DMSO-$d_6$) δ: 7.31-7.38 (m, 2 H), 7.47-7.56 (m, 4 H), 7.71-7.73 (m, 2 H), 7.77 (dd, J = 7.8, 1.5 Hz, 1 H), 7.83-7.96 (m, 7 H), 8.10 (dd, J = 1.8, 1.8 Hz, 1 H), 10.57 (brs, 1 H) |

TABLE 9-continued

| Compound No. | Physical Property |
|---|---|
| Compound 66 | Mp. 172-173° C. $^1$H NMR (DMSO-$d_6$) δ: 7.29 (dd, J = 8.2, 1.5 Hz, 1 H), 7.35 (dd, J = 8.0, 8.0 Hz, 1 H), 7.42-7.53 (m, 6 H), 7.68-7.71 (m, 4 H), 7.75 (dd, J = 7.9, 1.3 Hz, 1 H), 7.80-7.83 (m, 3 H), 7.86-7.88 (m, 2 H), 7.90-7.92 (m, 2 H), 7.96-7.98 (m, 2 H), 10.51 (brs, 1 H) |
| Compound 67 | Mp. 158-159° C. $^1$H NMR (DMSO-$d_6$) δ: 7.38 (dd, J = 8.0, 8.0 Hz, 1 H), 7.43-7.45 (m, 1 H), 7.78-7.79 (m, 1 H), 7.84-7.87 (m, 2 H), 8.01 (d, J = 8.0 Hz, 1 H), 8.11 (d, J = 8.0 Hz, 1 H), 8.21-8.23 (m, 1 H), 8.50-8.52 (m, 2 H), 8.55 (m, 1 H), 10.70 (brs, 1 H) |
| Compound 68 | Mp. 147-148° C. $^1$H NMR (DMSO-$d_6$) δ: 7.39 (dd, J = 8.0, 8.0 Hz, 1 H), 7.43-7.45 (m, 1 H), 7.78-7.79 (m, 1 H), 7.84 (dd, J = 8.0, 8.0 Hz, 1 H), 7.88 (s, 1 H), 8.00-8.02 (m, 3 H), 8.07 (d, J = 8.0 Hz, 1 H), 8.12-8.16 (m, 3 H), 10.71 (brs, 1 H) |
| Compound 69 | Mp. 165-166° C. $^1$H NMR (DMSO-$d_6$, 500 MHz) δ: 7.34-7.39 (m, 2 H), 7.78 (dd, J = 7.0, 2.5 Hz, 1 H), 7.88-7.91 (m, 2 H), 7.98 (d, J = 8.4 Hz, 2 H), 8.10 (d, J = 8.3 Hz, 2 H), 8.33-8.35 (m, 1 H), 8.50-8.52 (m, 1 H), 8.70 (dd, J = 2.0, 2.0 Hz, 1 H), 10.80 (brs, 1 H) |
| Compound 70 | Mp. 154-155° C. $^1$H NMR (DMSO-$d_6$) δ: 7.31-7.38 (m, 2 H), 7.42-7.46 (m, 1 H), 7.49-7.52 (m, 2 H), 7.73-7.75 (m, 2 H), 7.78 (dd, J = 7.7, 1.5 Hz, 1 H), 7.84 (s, 1 H), 7.89-7.90 (m, 2 H), 7.98-8.03 (m, 4 H), 8.11 (d, J = 8.0 Hz, 2 H), 10.53 (brs, 1 H) |

Test Example 1: Evaluation of the Suppressive Action for Expression of Gene of Factors Related to Inflammation of Bovine Cartilage (1) Incubation of Bovine Cartilage Pieces Each 6 to 8 cartilage pieces (diameter: 4 mm) of bovine metacarpophalangeal joint were placed into each well of a 24-well plate and incubated for one night in 1 mL of a basal medium in a $CO_2$ incubator which was set at 37° C. and 5% by volume of $CO_2$. After that, they were incubated for 2 hours in a basal medium containing 20 μmol/L of a test substance and, after addition of human recombinant IL-1α (3 ng/mL) thereto, they were incubated for 8 hours more. After completion of the incubation, the culture medium was discarded, an RNA stabilizer was added to the cartilage pieces, the mixture was incubated at 4° C. for one night and the cartilage pieces were finely cut using scissors, placed into micro-tubes and stored with freezing until the extraction of RNA therefrom.

(2) Extraction of RNA from Bovine Cartilage Pieces and Synthesis of cDNA

The cartilage pieces placed in the micro-tubes were pulverized using Tissue Lyser (QIAGEN) (at 25 Hz for 5 minutes; for two times), 1 mL of QIAzol Lysis Reagent (QIAGEN) was added thereto to suspend, 200 μL of chloroform was added thereto followed by mixing and the mixture was centrifuged (1500 rpm at 4° C.) to recover the supernatant liquid. Total RNA was extracted and purified using QIACube (QIAGEN) and RNeasy Micro Kit (QIAGEN). cDNA was prepared from the total RNA using Omniscript RT Kit (QIAGEN) and Oligo(dT)$_{12-18}$ Primer (Invitrogen).

(3) Measurement of the Action to the Gene Expression Level

The cDNA synthesized from the total RNA extracted in the above (2) was used to measure the gene expression level of the inflammation-related factors [IL-1β, IL-6, COX-2 and iNOS (inducible nitric oxide synthase)] by a conventional real time PCR method using a fluorescent dye SYBR GREEN I (Roche Diagnostics) by a Light Cycler LC 480 (the same). A calibration curve was prepared by dilution of a PCR product quantified by a DNA quantitation kit (PicoGreen dsDNA Quantitiation Kit (Molecular Probes)) to an extent of $10^2$~$10^7$ copies/μL. From each of the resulting measured data, copy numbers per 10000 copies of glyceroaldehyde-3-phosphate dehydrogenase (GAPDH) which was an internal standard were calculated.

An example of the results is shown in Table 10. The present compound exhibited a suppressive action to upregulation of gene expression of the inflammation-related factors induced by IL-1α and was noted to have a suppressive action for inflammation.

TABLE 10

| Test Substance | Copy Numbers per 10000 Copies of GAPDH | | |
|---|---|---|---|
| (n = 3) | IL-1β | IL-6 | COX-2 |
| Non-stimulated IL-1α | 65.8 | 2994.0 | 197.3 |
| Stimulated IL-1α | 809.9 | 24761.7 | 3254.2 |
| Compound 57 | 144.8 | 7749.8 | 1420.8 |
| Compound 58 | 157.8 | 9346.3 | 982.3 |
| Compound 60 | 170.6 | 9277.4 | 920.6 |
| Compound 68 | 175.1 | 16195.2 | 1655.9 |

Test Example 2: Evaluation of the Suppressive Action of Human Monocytic Cell Line (THP-1 Cells) to the Expression of Inflammation-Related Factors (1) Incubation of THP-1 Cells THP-1 cells were subjected to induction of differentiation for 72 hours with PMA (phorbol 12-myristate 13-acetate; 100 nM/L) and then the THP-1 cells (5×10$^5$ cells/mL) were incubated for 24 hours in a RPMI 1640+10% FCS culture solution in a 24-well plate. After that, a test substance was added so as to make the final concentration 12.5 μmol/mL followed by conducting the preincubation for 2 hours, a lipopolysaccharide (LPS) was then added thereto so as to make the final concentration 10 mg/mL and, after 3 hours, the cells were recovered.

(2) Extraction of RNA from THP-1 Cells and Synthesis of cDNA

QIAzol Lysis Reagent (QIAGEN) (1 mL) was added to the above to suspend, 200 μL of chloroform was added thereto followed by mixing and centrifugation (at 4° C. and 1500 rpm) was conducted whereby the supernatant liquid was recovered. Total RNA was extracted and purified by treating the supernatant liquid with QIACube (QIAGEN) and RNeasy Micro Kit (QIAGEN). cDNA was prepared from the total RNA using Omniscript RT kit (QIAGEN) and Oligo(dT)$_{12-18}$ Primer (Invitrogen).

(3) Measurement of the Action to the Gene Expression Level

Gene expression level of the inflammation-related factors [IL-1β, IL-6 and monocyte chemotactic protein (MCP)-1] was measured by a conventional real time PCR method using a fluorescent dye SYBR GREEN I (Roche Diagnostics) by Light Cycler LC 480 (the same) using cDNA synthesized from the total RNA extracted in the above (2). A calibration curve was prepared by diluting the PCR product quantified by PicoGreen dsDNA Quantitation kit (Molecular probes) (a DNA quantitation kit) to an extent of $10^2$~$10^7$ copies/μL. From each of the resulting quantified values, copy numbers per 10000 copies of GAPDH gene being an internal standard were calculated.

An example of the result is shown in Table 11. The present compound exhibited a suppressive action to upregulation of gene expression of the inflammation-related factors from THP-1 cells induced by LPS. Because of the above, the present compound was recognized to exhibit an anti-inflammatory action.

TABLE 11

| Test Substance (n = 3) | Copy Numbers per 10000 Copies of GAPDH | | |
|---|---|---|---|
| | IL-1β | IL-6 | MCP-1 |
| Non-stimulated LPS | 108.7 | 0 | 155.3 |
| Stimulated LPS | 34624.8 | 869.8 | 4805.3 |
| Compound 57 | 30318.3 | 49.0 | 1001.3 |
| Compound 58 | 31904.4 | 93.2 | 1040.9 |
| Compound 60 | 29872.3 | 275.2 | 1787.5 |
| Compound 68 | 24423.1 | 95.7 | 823.5 |

Test Example 3: Evaluation I of Suppressive Action to Gene Expression of a Fibrosis-Related Factor of Incubated Human Lung Fibroblasts (NHLF Cells)

(1) Incubation of NHLF Cells

NHLF cells were sown so as to make their amount $4 \times 10^4$ cells/well to each well of a 12-well plate and incubated to an extent of 80% confluent in a medium where fibroblast growth medium 2 supplement mix (FGM-2 SingleQuots, Lonza) was added to a fibroblast basal medium (FBM, Lonza). After that, incubation was conducted for 2 hours in a Dulbecco modified Eagle medium (DMEM) containing 25 μmol/L of a test substance and, after addition of tumor growth factor (TGF)-β thereto so as to make its final concentration 5 ng/mL, incubation was carried out for 24 hours more.

(2) Extraction of RNA from NHLF Cells and Synthesis of cDNA

QIAzol Lysis Reagent (QIAGEN) (1 mL) was added to the above to suspend, 200 μL of chloroform was added thereto followed by mixing and centrifugation (at 4° C. and 1500 rpm) was then conducted whereby the supernatant liquid was recovered. Total RNA was extracted and purified by treating the supernatant liquid with QIACube (QIAGEN) and RNeasy Micro Kit (QIAGEN). cDNA was prepared from the total RNA using Omniscript RT kit (QIAGEN) and Oligo(dT)$_{12-18}$ Primer (Invitrogen).

(3) Measurement of the Action to the Gene Expression Level

Gene expression level of the fibrosis-related factors [connective tissue growth factor (CTGF), α-smooth muscle actin (SMA), fibronectin, endothelin and type I collagen (Col 1)] was measured by a conventional real time PCR method using a fluorescent dye SYBR GREEN I (Roche Diagnostics) by Light Cycler LC 480 (the same) using cDNA synthesized from the total RNA extracted in the above (2). A calibration curve was prepared by diluting the PCR product quantified by PicoGreen dsDNA Quantitation kit (Molecular probes) (a DNA quantitation kit) to an extent of $10^2 \sim 10^7$ copies/μL. From each of the resulting quantified values, copy numbers per 10000 copies of GAPDH gene being an internal standard were calculated.

An example of the result is shown in Table 12. The present compound exhibited a suppressive action to upregulation of gene expression of the fibrosis-related factors from NHLF cells induced by TGF-β. Because of the above, the present compound was recognized to exhibit an anti-fibrotic action.

TABLE 12

| Test Substance (n = 3) | Copy Numbers per 10000 Copies of GAPDH | | | | |
|---|---|---|---|---|---|
| | CTGF | α-SMA | Fibronectin | Endothelin | Col 1 |
| Non-stimulated TGF-β | 2783.1 | 472.7 | 13407.0 | 0.8 | 2216.0 |
| Stimulated TGF-β | 28200.4 | 1868.0 | 46420.7 | 56.9 | 13759.6 |
| Compound 57 | 8963.4 | 1166.3 | 21220.7 | 8.2 | 9715.8 |
| Compound 58 | 5020.5 | 826.9 | 18665.2 | 7.6 | 5901.0 |
| Compound 60 | 13992.0 | 1324.8 | 30000.8 | 16.9 | 11388.1 |
| Compound 68 | 10441.5 | 1007.1 | 26090.7 | 6.4 | 8905.8 |

Test Example 4: Evaluation of Suppressive Action to NF-κB Activation (1) Preparation of Transient Expression Cells A preparation solution containing pGL4.32 [luc2P/NF-κB-RE/Hygro] (Promega) which is an NF-κB reporter vector, pGL4.74 [hRluc/TK] (Promega) which is a control vector and Lipofectamine LTX (Life Technologies) which is a gene transfer agent was added to human embryo kidney cells (HEK293T cells) sown onto a 100 ml dish whereupon there were prepared the cells which transiently express a reporter protein.

(2) Measurement of Luciferase Activity

After 24 hours from the gene transfer, transient expression cells were peeled off by treating with trypsin, sown on a poly-lysine coated white 96-well plate and incubated for one night. The test substance was added to as to make its final concentration 25 μml/mL and, after pre-incubating for 1 hour, TNF-α was added thereto so as to make its final concentration 10 ng/mL followed by incubating for 5 hours more. The cells were dissolved and the activities of a firefly luciferase and a renilla luciferase were measured. Rate of the luminescent intensity by addition of each drug to the luminescent intensity by stimulation with TNF-α were calculated.

An example of the result is shown in Table 13. The present compound exhibited a suppressive action to the activation of NF-κB induced by TNF-α. Because of the above, the present compound was recognized to exhibit an anti-inflammatory action.

TABLE 13

| Test Substance | Luminescent Intensity to Stimulated TNF-α (%) |
|---|---|
| Stimulated TNF-α | 100 |
| Compound 17 | 0.1 |
| Compound 57 | 7.5 |
| Compound 58 | 14.5 |
| Compound 60 | 15.7 |
| Compound 68 | 16.1 |

Test Example 5: Evaluation of the Suppressive Action to Lung Wet Weight Increase of Mice where Pulmonary Fibrosis was Induced by Bleomycin Bleomycin (2 mg/kg) was repeatedly injected intravenously for 5 days to ICR male mice. The mice were organized into 4 groups of normal control group, diseased control group, test substance-administered group and pirfenidone-administered group.

A test substance was suspended in 0.5 w/v % carboxymethyl cellulose sodium (CMC) and 50 mg/kg thereof was repeatedly administered per os with stirring twice daily for 2 weeks using an oral sonde for rats. Pirfenidone was suspended in 0.5 w/v % CMC and 200 mg/kg thereof was repeatedly administered per os with stirring twice daily for 2 weeks using an oral sonde for rats. To the normal control group and the diseased control group, 0.5 w/v % CMC was repeatedly administered per os according to the same administration schedule. After finishing the administration period, both lungs were excised from the mice and their wet weight was measured.

An example of the result is shown in Table 14. The present compound exhibited a suppressive action to fibrillization of lung in the model mice of pulmonary fibrosis induced by bleomycin and its degree was the same as that of pirfenidone approved as an anti-fibrotic agent in Japan. Because of the above, the present compound was recognized to exhibit an anti-fibrotic action.

TABLE 14

| Test Substance | Wet Lung Weight (g) |
| --- | --- |
| Normal control group (n = 12) | 205 |
| Diseased control group (n = 12) | 303 |
| Compound 60 (n = 12) | 250 |
| Pirfenidone (n = 11) | 242 |

Test Example 6: Evaluation of Suppressive Action to the Hyperalgesia in Lower Limbs and to the Lowering of Duration of Walking Time in Rats Suffering from Degenerative Intervertebral Disk Induced by Nicotine (1) Preparation of Rats Suffering from Degenerative Intervertebral Disk Induced by Nicotine After 16 days from the purchase, SD male rats were organized into normal control group and nicotine group in terms of body weight, 50% reaction threshold value (measuring method will be mentioned later) and duration of walking time and, after 17 days from the purchase, exposure to nicotine was started for a nicotine group. Nicotine was prepared into 344.8 mg/mL using a physiological saline solution, filled into an osmotic pressure pump and retained under the skin of waist of rats. After 21 days from the retaining, an osmotic pressure pump into which a freshly-prepared nicotine solution was filled was retained under the skin of rats of five groups except the normal control group. Nicotine was prepared into 357.0 ml/mL using a physiological saline solution, filled into an osmotic pressure pump and retained under the skin of waist of the SD male rats.

(2) Group Organization

After 13 days from exposure to nicotine, measurement of 50% reaction threshold value, duration of walking time and body weight were measured and a group organization was done into 6 groups of normal control group, diseased control group, compound 57-administered group, compound 58-administered group, compound 60-administered group and compound 68-administered group.

(3) Administration of a Test Substance

A test substance was suspended using 0.5 w/v % CMC and, together with stirring, 10 mL/kg of the suspension was repeatedly administered per os once daily after 14 to 52 or 53 days from the initiation of exposure to nicotine using an oral sonde for rats. To the normal control group and the diseased control group, 0.5 w/v % CMC was repeatedly administered per os in the same administration schedule and administration method.

(4) Measurement of 50% Reaction Threshold Value to Mechanical Stimulation (Von Frey Test)

A 50% reaction threshold value to mechanical stimulation was measured before the exposure to nicotine and after 41 days from the exposure to nicotine. The six groups of the rats mentioned in the above (2) were placed in a transparent acrylic gauge where the bottom is a metal wire, acclimated for about 3 minutes and a 50% reaction threshold value to mechanical stimulation was measured after 1 hour from the administration of a testing drug.

The measurement was conducted using a von Frey filament (manufactured by North Coast Medical Inc.) in accordance with a method of Chaplan, et al. (*Journal of Neuroscience Methods*, vol. 53, no. 1, pages 55 to 63, 1994) and a method of Dixon, et al. (*American Review of Pharmacology and Toxicology*, vol. 20, pages 441 to 462, 1980). Among 8 filaments [stimulation loads (g): 0.4, 0.6, 1.0, 2.0, 4.0, 6.0, 8.0 and 15.0], the operation was started from a filament of 2.0 g, then the filament was vertically applied to a paw sole for 2 to 3 seconds with such a force by which the filament was lightly bent and, when the hind limb showed a escape reaction, it was adopted as a positive reaction. When a positive reaction was noted, the same stimulation was applied using a filament of a lower strength in one grade while, when no reaction was noted, the same stimulation was applied using a filament of a higher strength in one grade, then the stage where the reaction changed from negative to positive or from positive to negative was adopted as the first two reactions and, after that, stimulation was conducted for continued four times by an up-down method. A 50% reaction threshold value to mechanical stimulation was measured using the reaction for the stimulation for six times in total and a mean value in each of the groups was calculated. Incidentally, when the operation was done until the stimulation of 15.0 g without the positive reaction and, on the other hand, when the positive reaction continued to 0.4 g, then 15.0 g and 0.25 g were adopted as the threshold value (threshold value for the pain) therefor, respectively.

(5) Measurement of Duration of Walking Time

Before the exposure to nicotine and after 48 days from the initiation of the exposure to nicotine, duration of waling time of rats was measured using a rotor rod for both rats and mice. A rotating speed was adjusted in such a manner that, when rotation was started in constant acceleration from the state where a rotor stopped, it reached 15 rotations per minute after 300 seconds. A rat was placed on a rotor which was in a stopped state, then the rotor was rotated, the time until the rat dropped was measured (300 seconds in maximum) and a mean value of three runs was determined.

An example of results of the above (4) and (5) is shown in Table 15. The present compound showed a strong suppressive action to the hyperalgesia in lower limbs and the gait disorder by exposure to nicotine. Because of the above, the present compound was recognized to have a suppressive action to the hyperalgesia and the gait disorder caused by degenerative intervertebral disk disease.

TABLE 15

| Test Substance (n = 8) | Threshold Value for Pain (g) | Duration of Walking Time (seconds) |
| --- | --- | --- |
| Normal control group | 15.0 | 274.1 |
| Diseased control group | 4.6 | 147.7 |

TABLE 15-continued

| Test Substance (n = 8) | Threshold Value for Pain (g) | Duration of Walking Time (seconds) |
|---|---|---|
| Compound 57 | 7.5 | 187.3 |
| Compound 58 | 6.7 | 210.9 |
| Compound 60 | 9.6 | 208.4 |
| Compound 68 | 7.6 | 189.2 |

Test Example 7: Evaluation II of Suppressive Action to Gene Expression of the Fibrosis-Related Factor of the Incubated Human Lung Fibroblasts (NHLF Cells)

(1) Incubation of NHLF Cells

NHLF cells were sown so as to make their amount $5 \times 10^4$ cells/well to each well of a 12-well plate and incubated to an extent of 80% confluent in a medium where fibroblast growth medium 2 supplement mix (FGM-2 SingleQuots, Lonza) was added to a fibroblast basal medium (FBM, Lonza). After that, incubation was conducted for 2 hours in a DMEM medium containing 30 µM of a test substance, 200 µg/mL of pirfenidone, 30 µM of dexamethasone (DEX), 1.0 µM of TPCA-1 or 10 µM of fluticasone propionate (FP) and, after TGF-β was added thereto so as to make its final concentration 0.5 ng/mL, incubation was carried out for 4 hours more.

With regard to the extraction of RNA from NHLF cells, the synthesis of cDNA from RNA and the action of the test substance to gene expression of fibrosis-related factors [CFGF, TGF-β1, fibronectin and Col 1], the tests were carried out in the same manners as in (2) and (3) of the above Test Example 3.

An example of the result is shown in Table 16. The present compound exhibited a more suppressive action to upregulation of gene expression of the fibrosis-related factors from NHLF cells inducted by TGF-β than pirfenidone, DEX and FP. Because of the above, the present compound was recognized to exhibit an excellent anti-fibrotic action.

TABLE 16

| Test Substance | Copy Numbers per 10000 Copies of GAPDH | | | |
|---|---|---|---|---|
| (n = 4) | CTGF | TGF-β1 | Fibronectin | Col 1 |
| Non-stimulated TGF-β | 86.9 | 355.7 | 2813.8 | 696.4 |
| Stimulated TGF-β | 270.1 | 938.6 | 2350.1 | 1067.6 |
| Compound 58 | 115.8 | 704.5 | 1827.5 | 525.6 |
| Compound 60 | 119.0 | 707.1 | 1446.2 | 650.6 |
| Pirfenidone | 180.6 | 962.5 | 1689.7 | 1027.6 |
| TPCA-1 | 461.2 | 886.9 | 3757.9 | 840.4 |
| DEX | 1010.1 | 546.9 | 4314.6 | 610.7 |
| FP | 1166.8 | 450.6 | 3603.2 | 593.3 |

INDUSTRIAL APPLICABILITY

As shown in the above pharmacological test results, the present invention exhibits an excellent suppressive action for the expression of inflammation-related factor and a suppressive action for the expression of fibrosis-related factor and, even in animal experiments, it exhibits an excellent suppressive action for pulmonary fibrillization in a pulmonary fibrosis model and also exhibits an excellent suppressive action for hyperalgesia and for gait disorder in a degenerative intervertebral disk disease model. Accordingly, the present invention is highly useful as a preventive or therapeutic agent for inflammatory diseases or degenerative intervertebral disk diseases.

The invention claimed is:

1. A method for therapeutically treating an inflammatory disease and/or degenerative intervertebral disk disease in a subject, comprising
administering to the subject an effective amount of a coumarin derivative represented by formula (I), or a pharmaceutically acceptable salt or hydrate thereof to therapeutically treat an inflammatory disease and/or degenerative intervertebral disk disease:

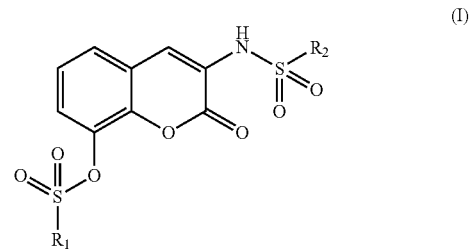

where:
each of $R_1$ and $R_2$ is independently selected from the group consisting of (a) phenyl optionally substituted with alkoxy, alkyl, cyano, nitro, hydroxy, trifluoromethyl, amino, carboxy, alkoxycarbonyl, phenyl, or one or two halogen(s), (b) pyridyl, (c) alkyl, and (d) thienyl.

2. The method according to claim 1, where each of $R_1$ and $R_2$ is independently phenyl optionally substituted with alkoxy, alkyl, cyano, nitro, hydroxy, trifluoromethyl, amino, carboxy, alkoxycarbonyl, phenyl, or one or two halogen(s).

3. The method according to claim 2, where each of $R_1$ and $R_2$ is independently phenyl substituted with alkoxy, alkyl, cyano, nitro, hydroxy, trifluoromethyl, amino, carboxy, alkoxycarbonyl, phenyl, or one or two halogen(s).

4. The method according to claim 3, where each of $R_1$ and $R_2$ is phenyl substituted with trifluoromethyl.

5. The method according to claim 3, where one of $R_1$ and $R_2$ is phenyl substituted with trifluoromethyl.

6. The method according to claim 5, where the other of $R_1$ and $R_2$ is phenyl substituted with halogen.

7. The method according to claim 6, wherein the halogen is bromine.

8. The method according to claim 1, wherein the inflammatory disease is chronic obstructive pulmonary disease or pulmonary fibrosis.

9. The method according to claim 1, wherein the coumarin derivative or pharmaceutically acceptable salt or hydrate thereof is administered to the subject orally.

10. The method according to claim 1, wherein the coumarin derivative or pharmaceutically acceptable salt or hydrate thereof is administered to the subject by injection.

11. The method according to claim 1, wherein the coumarin derivative or pharmaceutically acceptable salt or hydrate thereof is administered to the subject by external application.

12. The method according to claim 11, wherein the coumarin derivative or pharmaceutically acceptable salt or hydrate thereof is inhaled by the subject.

13. The method according to claim 12, wherein the coumarin derivative or pharmaceutically acceptable salt or hydrate thereof is administered by transpulmonary administration.

* * * * *